United States Patent [19]
Wai et al.

[11] Patent Number: 5,753,650
[45] Date of Patent: May 19, 1998

[54] INHIBITORS OF FARNESYL-PROTEIN TRANSFERASE

[75] Inventors: John S. Wai, Harleysville; J. Christopher Culberson, Hatfield; Samuel L. Graham, Schwenksville, all of Pa.

[73] Assignee: Merck & Co., Inc., Rahway, N.J.

[21] Appl. No.: 737,191

[22] PCT Filed: May 16, 1995

[86] PCT No.: PCT/US95/06286

§ 371 Date: Nov. 6, 1996

§ 102(e) Date: Nov. 6, 1996

[87] PCT Pub. No.: WO95/32191

PCT Pub. Date: Nov. 30, 1995

Related U.S. Application Data

[63] Continuation of Ser. No. 247,122, May 20, 1994, abandoned.

[51] Int. Cl.$^6$ ............ A61K 31/55; C07D 243/14; C07D 243/24
[52] U.S. Cl. ............ 514/221; 540/509
[58] Field of Search ............ 540/509; 514/221

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |
| 5,324,726 | 6/1994 | Bock et al. | 514/221 |
| 5,326,773 | 7/1994 | deSolms et al. | 514/336 |
| 5,340,828 | 8/1994 | Graham et al. | 514/357 |
| 5,352,705 | 10/1994 | Deana, deceased et al. | 514/630 |
| 5,504,212 | 4/1996 | deSolms et al. | 546/336 |
| 5,532,359 | 7/1996 | Marster, Jr. et al | 540/522 |

FOREIGN PATENT DOCUMENTS

| | | |
|---|---|---|
| 0 456 180 A1 | of 0000 | European Pat. Off. |
| WO 91/16340 | of 0000 | WIPO |
| WO 94/26723 | of 0000 | WIPO |

OTHER PUBLICATIONS

J. of Biol. Chem, vol. 266, No. 24, pp. 15575–15578 (1991), by J. L. Goldstein, et al.
Science, vol. 260, pp. 1934–1937 (1993), by N. E. Kohl, et al.
Science, vol. 260, pp. 1937–1942 (1993), by G. L. James, et al.
J. of Biol. Chem., vol. 268, No. 11, pp. 7617–7620 (1993), J. B. Gibbs, et al.
Biochemistry, vol. 31, pp. 3800–3807 (1992), by D. L. Pompliano, et al.
J. Org. Chem., vol. 52, pp. 3232–3239 (1987), by M. G. Bock, et al.
J. of Biol. Chem., vol. 369, No. 44, pp. 27706–27713 (1994), by G. L. James, et al.
Science, vol. 260, pp. 1937–1942 (25 Jun. 1993), by G. L. James, et al.
Nature Medicine, vol. 1, No. 8, pp. 792–797 (Aug. 1995), by N. E. Kohl, et al.
Proc. Natl. Acad. Sci. USA, vol. 91, pp. 9141–9145 (1994), by N. E. Kohl, et al.
Current Biol., vol. 3, pp. 770–772 (1993), by J. F. Hancock.
TIBS, vol. 18, pp. 349–353 (1993), by F. Tamanoi.
Cell, vol. 77, pp. 175–178 (Apr. 1994), by J. B. Gibbs, et al.
Cancer Res., vol. 55, pp. 5302–5309 (1995), by L. Sepp–Lorenzino, et al.
J. of Biol. Chem., vol. 270, No. 11, pp. 6221–6226 (1995), by G. L. James, et al.

Primary Examiner—Mukund J. Shah
Assistant Examiner—Bruck Kifle
Attorney, Agent, or Firm—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and treatment of cancer, which compound has the structure;

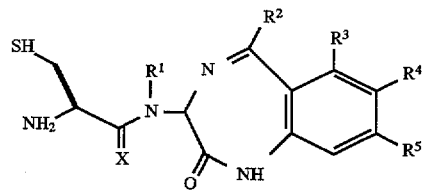

or a pharmaceutically acceptable salt or disulfide thereof and wherein the variables are as defined in the specification.

6 Claims, No Drawings

INHIBITORS OF FARNESYL-PROTEIN TRANSFERASE

This application is a 371 of PCT/US95/06286 filed May 16, 1995, which is a continuation of application Ser. No. 08/247,122 filed May 20, 1994 now abandoned.

BACKGROUND OF THE INVENTION

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989)). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., Cell 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989)); Hancock et al., Cell 57: 1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J.Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., Cell, 62: 81–88 (1990); Schaber et al., *J. Biol. Chem.*, 265:14701–14704 (1990); Schafer et al., Science, 249: 1133–1139 (1990); Manne et al., *Proc. Natl. Acad. Sci USA*, 87: 7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634 (1989)). Cytosol localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of Ras, and other cellular proteins, with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., *PNAS*, 88:732–736 (1991)). It was, however, disclosed that tetrapeptides which further contained a cyclic amino acid residue, such as proline, had greatly reduced inhibitory activity when compared to tetrapeptides not containing a cyclic amino acid (Reiss et al., (1991). Tetrapeptide inhibitors may inhibit while serving as alternate substrates for the Ras farnesyltransferase enzyme, or may be purely competitive inhibitors (U.S. Pat. No. 5,141,851, University of Texas).

Recently, it has been demonstrated that certain inhibitors of farnesyl-protein transferase selectively block the processing of Ras oncoprotein intracellularly (N. E. Kohl et al. *Science*, 260:1934–1937 (1993) and G. L. James et al. *Science*, 260:1937–1942 (1993).

Among the inhibitors of farnesyl protein transferase that have been described in the art are benzodiazepine derivatives that mimic the CAAX motif of a prenylated protein (James, et al., Science 1993, 260, 1937–1942). These compounds are potent inhibitors of FPTase. However, the compounds described by James, et al. are carboxylic acids which have relatively poor activity as inhibitors of farnesylation in intact cells. To render such compounds useful for inhibition of the transformed phenotype of a cancer cell, esterification of the C-terminal carboxylate is required. Such a prodrug strategy significantly complicates the clinical application of an FPTase inhibitor by adding additional variables to its pharmokinetic and pharmodynamic analysis.

It is, therefore, an object of this invention to develop non-peptide compounds which will inhibit farnesyl-protein transferase and the farnesylation of the oncogene protein Ras. It is a further object of this invention to develop chemotherapeutic compositions containing the compounds of this invention, and methods for producing the compounds of this invention.

It is also the object of the invention to provide a FPTase inhibitor having a benzodiazepine structure wherein the C-terminal dipeptide moiety of previously described benzodiazepine FPTase inhibitors has been deleted while retaining significant FPTase inhibitory activity. Such inhibitors lack carboxylic acid moieties and are therefore devoid of the liabilities associated with the necessity of developing a prodrug.

SUMMARY OF THE INVENTION

The present invention includes benzodiazepine analogs which inhibit farnesyl-protein transferase (FPTase) and the farnesylation of the oncogene protein Ras, chemotherapeutic compositions containing the compounds of this invention, and methods for producing the compounds of this invention. It has been surprisingly found that these non-peptidyl analogs show FPTase inhibitory activity which is comparable to previously known tetrapeptide analogs.

The compounds of this invention are illustrated by the formula I:

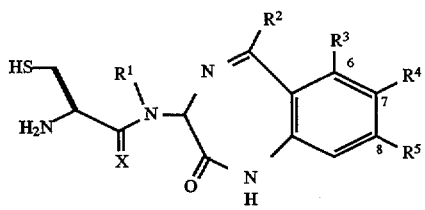

DETAILED DESCRIPTION OF THE INVENTION

The compounds of this invention are useful in the inhibition of farnesyl-protein transferase and the farnesylation of the oncogene protein Ras. In an embodiment of this invention, the inhibitors of farnesyl-protein transferase are illustrated by the formula I:

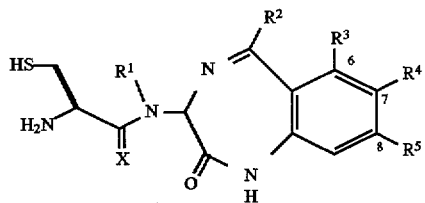

wherein:

$R^1$ is selected from: H or $C_{1-4}$ alkyl;

$R^2$ is selected from: H; unsubstituted or substituted $C_{1-4}$ alkyl, unsubstituted or substituted $C_{3-6}$ cycloalkyl, unsubstituted or substituted heterocycle, unsubstituted or substituted aryl, wherein the substituent is selected from:

a) $C_{1-4}$ alkoxy,
b) aryl or heterocycle,
c) halogen,
d) HO, e) ![structure] $R^6$, or f) $-SO_2R^6$;

$R^3$, $R^4$ and $R^5$ are independently selected from: H, $C_{1-4}$ alkyl, and halogen; provided that $R^2$ is H when $R^3$ is other than H; $R^6$ is $C_{1-4}$ alkyl or aralkyl;

X is O or $H_2$ or the pharmaceutically acceptable salts or disulfides thereof.

In a more preferred embodiment of this invention, the inhibitors of farnesyl-protein transferase are illustrated by the formula I:

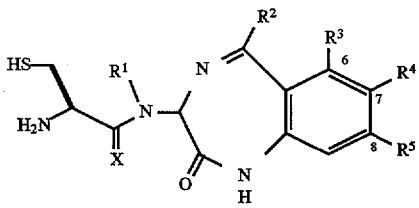

wherein:

$R^1$ is $C_{1-4}$ alkyl;

$R^2$ is selected from: H; unsubstituted or substituted $C_{1-4}$ alkyl, unsubstituted or substituted $C_{3-6}$ cycloalkyl or unsubstituted or substituted aryl, wherein the substituent is selected from:

a) $C_{1-4}$ alkoxy,
b) aryl or heterocycle,
c) halogen,
d) HO, e) ![structure] $R^6$, or f) $-SO_2R^6$;

$R^3$, $R^4$ and $R^5$ are independently selected from: H, $C_{1-4}$ alkyl, and halogen; provided that $R^2$ is H when $R^3$ is other than H;

$R^6$ is $C_{1-4}$ alkyl or aralkyl;

X is O or $H_2$ or the pharmaceutically acceptable salts or disulfides thereof.

Specific compounds of this invention are as follows:

3-[2(S)-amino-3-mercaptopropionyl-N-methylamino]-2, 3-dihydro-2-oxo-5-phenyl-1H-1,4-benzodiazepine 3-[2(S)-amino-3-mercaptopropionyl-N-methylamino]-2, 3-dihydro-2-oxo-5-(2-naphthyl)-1H-1,4-benzodiazepine 3-[2(S)-amino-3-mercaptopropionyl-N-methylamino]-2, 3-dihydro-2-oxo-5-(2-naphthyl)-1H-1,4-benzodiazepine 3-[2(S)-amino-3-mercaptopropionyl-N-methylamino]-7, 8-dimethyl-2,3-dihydro-2-oxo-5-phenyl-1H- 1,4-benzodiazepine 3-[N-2(S)-amino-3-mercaptopropionyl-N-methylamino]-2,3-dihydro-6-naphthylmethyl-2-oxo-1H-1,4-benzodiazepine 3-[2(S)-amino-3-mercaptopropionyl-N-methylamino]-2, 3-dihydro-2-oxo-5-(8-quinolinyl)-1H-1,4-benzodiazepine 3-[2(S)-amino-3-mercaptopropionyl-N-methylamino]-2, 3-dihydro-2-oxo-5-(2,3-dimethylphenyl)-1H-1,4-benzodiazepine or the pharmaceutically acceptable salts or disulfides thereof.

A preferred compound of this invention is the following inhibitor:

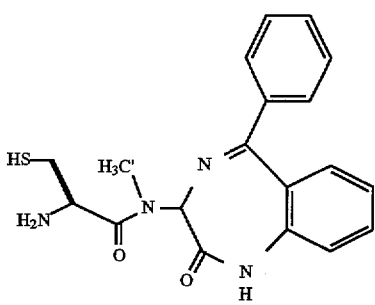

3-[2(S)-amino-3-mercaptopropionyl-N-methylamino]-2,3-dihydro-2-oxo-5-phenyl-1H-1,4-benzodiazepine or the pharmaceutically acceptable salts or disulfides thereof.

The compounds of the present invention may have asymmetric centers and occur as racemates, racemic mixtures, and as individual diastereomers, with all possible isomers, including optical isomers, being included in the present invention. The present invention further includes all disulfides of the claimed compounds, derived from two of the same compounds. When any variable (e.g. aryl, heterocycle, alkyl, aryl, etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5-to 7-membered monocyclic or stable 8to 11-membered bicyclic or stable 11–15 membered tricyclic heterocyclic ring which is either saturated or unsaturated, and which consists of carbon atoms and from one to four heteroatoms selected from the group consisting of N, O, and S(O)m (wherein m=0, 1 or 2), and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized by methods well know in the pharmaceutical arts, and the additional methods described below. Standard methods of benzodiazapine synthesis are disclosed, for example, in the following publications: Evans, B. E. et al., *J. Med. Chem.* 31:2235 (1988) and Block, M. G. et al., *J. Org. Chem.*, 52: 3232 (1987). The teachings of these works are hereby incorporated by reference.

Abbreviations used in the description of the chemistry and in the Examples that follow are:
Ac$_2$O Acetic anhydride;
Boc t-Butoxycarbonyl;
BOP bis(2-oxo-3-oxazolidinyl)phosphonic chloride
CAN cerric ammonium nitrate
CBz benzyloxycarbonyl
DBU 1,8-diazabicyclo[5.4.0]undec-7-ene;
DMAP 4-Dimethylaminopyridine;
DME 1,2-Dimethoxyethane;
DMF Dimethylformamide;
EDC 1-(3-dimethylaminopropyl)-3-ethyl-carbodiimide hydrochloride;
HOBT 1-Hydroxybenzotriazole hydrate;
Et$_3$N Triethylamine;
EtOAc Ethyl acetate.
FAB Fast atom bombardment;
HOOBT 3-Hydroxy-1,2,2-benzotriazin-4(3H)-one;
HPLC High-performance liquid chromatography;
KHMDS Potassium bis(trimethylsilyl)amide
MCPBA m-Chloroperoxybenzoic acid;
MsCl Methanesulfonyl chloride;
NaHMDS Sodium bis(trimethylsilyl)amide
PMB p-Methoxybenzyl
Py Pyridine;
TFA Trifluoroacetic acid;
THF Tetrahydrofuran;
Tr Trityl, triphenylmethyl.

The compounds of this invention are prepared as illustrated by Reaction Schemes A and B, in addition to other standard manipulations such as ester hydrolysis, cleavage of protecting groups, etc., as may be known in the literature or exemplified in the experimental procedures.

REACTION SCHEME A
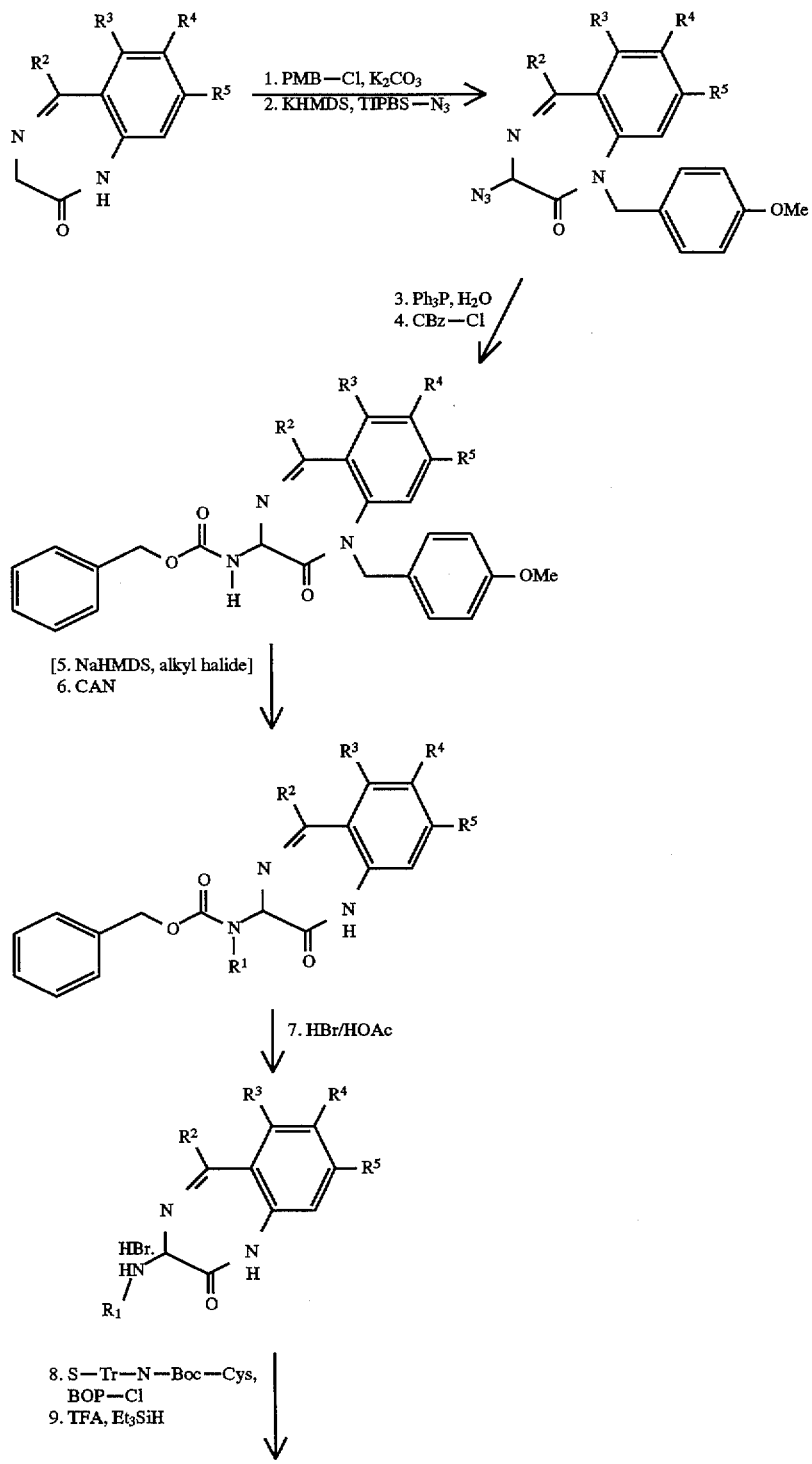

-continued
REACTION SCHEME A

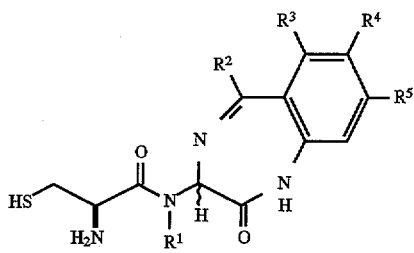

separation of diastereomers

REACTION SCHEME B

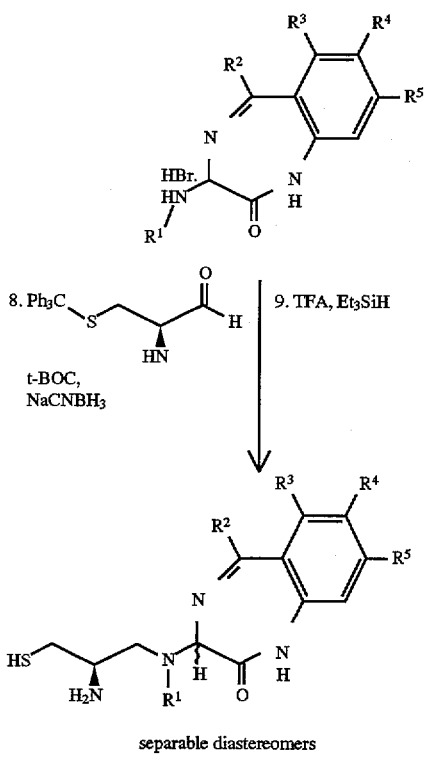

separable diastereomers where $R^1$, $R^2$, $R^3$, $R^4$ and $R^5$ are as previously defined, including their protected forms compatible with the reaction conditions shown, for example, the triphenylmethyl (trityl) protected side chain of cysteine.

Specifically, Reaction Scheme A shows the preparation of compounds of the instant invention wherein the attachment of the cysteine residue to the aminobenzodiazepine is through an amide bond (wherein variable "X"=O). As seen in the Scheme, the nitrogen attached to the benzodiazepine may be optionally alkylated prior to the attachment of the cysteine residue. Typically, the final diastereomeric mixture of products can be separated by chromatographic techniques well known in the art; however it is understood that, when such a separation of isomers is not possible, racemic mixtures of the compounds of the instant invention are also therapeutically useful.

Reaction Scheme B shows the preparation of compounds of the instant invention wherein the attachment of the cysteine residue to the aminobenzodiazepine is through a reduced amide bond (wherein variable "X"=$H_2$).

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

EXAMPLES

Examples provided are intended to assist in a further understanding of the invention. Particular materials employed, species and conditions are intended to be further illustrative of the invention and not limitative of the reasonable scope thereof.

Example 1

Preparation of 3-[N-2(S)-amino-3-mercaptopropionyl-N-methyl]amino-2,3-dihydro-2-oxo-5,-phenyl-1H-1,4-benzodiazepine (Compound 1)

Step 1 Preparation of 2,3-dihydro-1-[4-methoxybenzyl]-2-oxo-5-phenyl-1H-1,4-benzodiazepine A mixture of 2,3-dihydro-2-oxo-5-phenyl-1H-1,4-benzodiazepine (13.43 g, 57 mmmol, prepared as described by Mark G. Bock et al in *Journal of Organic Chemistry*, Vol. 52, pp. 3232–3239, year 1987), 4-methoxybenzyl chloride (12.6 mL, 62.5 mmol) and potassium carbonate (15.7 g, 114 mmol) in N,N-dimethylformamide (130 mL) was heated at 60° C. overnight under an atmosphere of argon. The resultant slurry was concentrated and the residue was treated with ethyl acetate and water. The organic extract was separated, washed twice with brine, dried over anhydrous magnesium sulfate, filtered and concentrated under vacuo. The residue was subjected to column chromatography on silica gel eluting with 1:1 ethyl acetate and hexane. Collection and concentration of appropriate fractions provided 2,3-dihydro-1-[4-methoxybenzyl]-2-oxo-5-phenyl-1H-1,4-benzodiazepine.

Step 2 Preparation of (±)3-azido-2,3-dihydro-1-[4-methoxybenzyl]-2-oxo-5-phenyl-1H-1,4-benzodiazepine To a clear colorless cold (−78° C.) solution of 2,3-dihydro-1-[4-methoxybenzyl]-2-oxo-5-phenyl-1H-1,4-benzodiazepine (5.33 g, 15 mmol in anhydrous tetrahydrofuran (THF) (100 mL) under an atmosphere of dry argon, a solution of potassium bis(trimethylsilyl)amide in toluene (33 mL, 0.5 M, 164 mmol) was added over a period of 5 minutes. The resultant deep red solution was stirred at −78° C. for 20 minutes and was treated with a solution of 2,4,6-triisopropylbenzenesulfonyl azide (5.79 g, 18.7 mmol) in THF (20 mL) over a period of 2 minute. The resultant pale golden solution was stirred at −78° C. for 10 minutes and treated with 4 mL of glacial acetic acid. The mixture was warmed up to room temperature and stirred for additional 1.5 hour. The mixture was diluted with dichloromethane (500 mL) and washed successively with water, aqueous sodium bicarbonate, and brine. The organic solution separated was dried over anhydrous magnesium sulfate, filtered and concentrated under vacuo. The residue was subjected to column chromatography on silica gel eluting with 1.5% methanol in chloroform. Collection and concentration of appropriate fraction provided the azido compound.

Step 3 Preparation of (±) 3-amino-2,3-dihydro-1-[4-methoxybenzyl]2-oxo-5-phenyl-1H-1,4-benzodiazepine A solution of (±) 3-azido-2,3-dihydro-1-[4-methoxybenzyl]-2-oxo-5-phenyl-1-1,4-benzodiazepine (5.03 g, 12.6 mmol), triphenylphosphine (4.3 g, 16.4 mmol), and water (2.3 mL, 12.6 mmol) in THF (80 mL) was stirred at room temperature overnight. The resultant mixture was concentrated onto silica gel (20 g) and the residue was loaded onto a column of silica gel saturated with 5% methanol in chloroform. Elution with 5% methanol in chloroform provided the amino compound.

Step 4 Preparation of (±) 3-[N-carbobenzyloxy]amino-2,3-dihydro-1-[4-methoxybenzyl]-2-oxo-5-phenyl-1H-1,4-benzodiazepine To a cold (0° C.) solution of (±) 3-amino-2,3 -dihydro-1-[4-methoxybenzyl]-2 -oxo-5-phenyl-1H-1,4-benzodiazepine (3.2 g, 8.6 mmol), diisopropylethylamine (1.8 mL, 10 mmol), 4-N,N-dimethylaminopyridine (150 mg) in dichloromethane (43 ML), benzyl chloroformate (1.48 mL, 10 mmol) was added. The resultant solution was stirred at room temperature for 2 hours, washed successively with aqueous sodium bicarbonate and brine, dried over anhydrous magnesium sulfate, filtered and concentrated under vacuo. The residue was subjected to column chromatography on silica gel eluting with dichloromethane. Collection and concentration of appropriate fractions provided the benzodiazepine.

Step 5 Preparation of (±) 3-[N-carbobenzyloxy-N-methyl]amino-2,3-dihydro-1-[4-methoxybenzyl]-2-oxo-5-phenyl-1H-1,4-benzodiazepine To a cold (−78° C.) solution of (±) 3-[N-carbobenzyloxy] amino-2,3-dihydro-1-[4-methoxybenzyl]-2-oxo-5-phenyl-1H-1, 4-benzodiazepine (1.0 g, 1.98 mmol, dried by dissolving in a mixture of dichloromethane and benzene, concentrated under reduced pressure and stored under vacuo over $P_2O_5$) in THF (27 mL) under an atmosphere of dry argon, a solution of sodium bis(trimethylsilyl)amide in THF (2.4 mL, 2.4 mmol) was added and stirred at −78° C. for 1 hour. Iodomethane (0.37 mL, 4 mmol, dried and hydrogen iodide removed by passing through a small plug of freshly activated basic alumina) was added and the mixture stirred at −78° C. for 1 hour and at room temperature for 2 hours. The resultant solution was diluted with diethyl ether, washed with brine, dried over anhydrous magnesium sulfate, filtered and concentrated under vacuo. The residue was subjected to column chromatography on silica gel eluting with 40% ethyl acetate in hexane. Collection and concentration of appropriate fractions provided the methylated compound.

Step 6 Preparation of (±) 3-[N-carbobenzyloxy-N-methyl]amino-2,3-dihydro-2-oxo-5-phenyl-1H-1,4-benzodiazepine A suspension of (±) 3-[N-carbobenzyloxy-N-methyl] amino-2,3-dihydro-1-[4-methoxybenzyl]-2-oxo-5-phenyl-1H-1,4-benzodiazepine (0.78 g, 1.5 mmol) in a mixture of acetonitrile (4.4 mL), water (1.6 mL) and ammonium cerium (IV) nitrate (4.0 g) was vortexed vigorously for 5 minutes. The resultant clear orange solution was stirred at room temperature for 20 minutes and add dropwisely into a mixture of saturated sodium potassium tartrate solution (52 mL), water (35 mL), and ethyl acetate (250 mL). The resultant mixture was stirred at room temperature for 1.5 hour, and the organic extract was washed with brine, dried over anhydrous magnesium sulfate, filtered and concentrated under vacuo. The residue was subjected to column chromatography on silica gel eluting with 2% methanol in chloroform. Collection and concentration of appropriate fraction provided the titled product.

Step 7 Preparation of (±) 2,3-dihydro-2-oxo-3-N-methylamino-5-phenyl-1H-1,4-benzodiazepine hydrobromide To a solution of (±) 3-[N-carbobenzyloxy-N-methyl] amino-2,3-dihydro-2-oxo-5-phenyl-1H-1,4-benzodiazepine (293 mg, 0.73 mmol) in dichloromethane (6 mL), 2 mL of 30% HBr in acetic acid was added. The resultant solution was stirred at room temperature for 2 hours and treated with anhydrous diethyl ether (80 mL). The pale yellow solid that precipitated out of solution was filtered, washed with diethyl ether (3×20 mL), and dried under vacuo for 2 hours. The crude product was used in the following step without further purification.

Step 8 Preparation of 3{N-[2(S)-N-tert-(butyloxy)carbonylamino-3-S-triphenylmethylmercaptopropionyl]-N-methyl}amino-2,3-dihydro-2-oxo-5-phenyl-1H-1,4-benzodiazepine A mixture of (±) 2,3-dihydro-2-oxo-3-N-methylamino-5-phenyl-1H-1,4-benzodiazepine hydrobromide (42 mg, 121 μmol), N-Boc-S-Trityl-L-Cysteine (142 mg, 306 μmol), diisopropylethylamine (76 μL, 436 μmol) in anhydrous dichloromethane (2 mL) at 0° C. was treated with bis(2-oxo-3-oxazolidinyl)-phosphinic chloride (77.2 mg, 303 μmol) and kept at 0° C. overnight. The resulting solution was diluted with dichloromethane (20 mL) and washed successively with aqueous sodium bicarbonate and brine, dried over anhydrous magnesium sulfate, filtered, and concentrated. The residue was subjected to column chromatography on silica gel. Collection and concentration of appropriate fractions provided a 1:1 mixture of the required diastereomeric products.

Step 9 Preparation of 3-[N-2(S)-amino-3-mercaptopropionyl-N-methyl]amino-2,3-dihydro-2-oxo-5-phenyl-1H-1,4-benzodiazepine (Compound 1)

To a solution of 3 {N-[2(S)-N-tert-(butyloxy)carbonylamino-3-S-triphenylmethylmercaptopropionyl]-N-methyl}amino-2,3-dihydro-2-oxo-5-phenyl-1H-1,4-benzodiazepine (65 mg, 82 μmol) in dichloromethane (3 mL) at room temperature, trifluoroacetic acid (1 mL) was added. The resultant intensely yellow solution was titrated to colorless by dropwise addition of triethylsilane (~82 μmol). The product mixture was concentrated, and partitioned with 0.1% aqueous trifluoroacetic acid (20 mL) and hexane (20 mL). The organic layer was decanted and the aqueous layer repeatedly extracted with hexane (4 times). The aqueous solution was lyophilized overnight and the residue (36 mg, 1:1 mixture of diastereomers) was subjected to high pressure liquid chromatography on a C-18 Vydac protein-peptide column (1 in) eluting with 95% (0.1% trifluoroacetic acid in water)/5% (0.09% trifluoroacetic acid in acetonitrile to 5% (0.1% trifluoroacetic acid in water)/95% (0.09% trifluoroacetic acid in acetonitrile)—50 minutes linear gradient. Pure fractions of each diastereomers were collected and lyophilized to provided the pure faster and slower eluting diastereomers.

Anal. Calcd for $C_{19}H_{20}N_4O_5 \cdot 1.25$ $CF_3COOH \cdot 0.25$ $H_2O$: C, 50.10; H, 4.25; N, 10.87. Found: C, 50.12; H, 4.28; N, 10.91 for the slower eluting isomer.

Example 2

Preparation of 3-[N-2(S)-amino-3-mercaptopropionyl]amino-2,3-dihydro-2-oxo-5-phenyl-1H-1,4-benzodiazepine (Compound 2)

Step 1 Preparation of (±) 3-[N-carbobenzyloxy]amino-2,3-dihydro-2-oxo-5-phenyl-1H-1,4-benzodiazepine A suspension of (±) 3-[N-carbobenzyloxy]amino-2,3-dihydro-1-[4-methoxybenzyl]-2-oxo-5-phenyl-1H-1,4-benzodiazepine (0.58 g, 1.15 mmol, from step 5 of Example 1) in a mixture of acetonitrile (3.3 mL), water (1.2 mL) and ammonium cerium(IV) nitrate (3.1 g) was vortexed vigorously for 5 minutes. The resultant clear orange solution was stirred at room temperature for 20 minutes and add dropwisely into a mixture of saturated sodium potassium tartrate solution (40 mL), water (27 mL), and ethyl acetate (190 mL). The resultant mixture was stirred at room temperature for 1.5 hour, and the organic extract was washed with brine, dried over anhydrous magnesium sulfate, filtered and concentrated under vacuo. The residue was subjected to column chromatography on silica gel eluting with 2% methanol in chloroform. Collection and concentration of appropriate fraction provided the title compound.

Step 2 Preparation of (±) 2,3-dihydro-2-oxo-amino-5-phenyl-1H-1,4-benzodiazepine hydrobromide To a solution of (±) 3-[N-carbobenzyloxy]amino-2,3-dihydro-2-oxo-5-phenyl-1H-1,4-benzodiazepine (293 mg, 0.73 mmol) in dichloromethane (6 mL), 2 mL of 30% HBr in acetic acid was added. The resultant solution was stirred at room temperature for 2 hours and treated with anhydrous diethyl ether (80 mL). The pale yellow solid that precipitated out of solution was filtered, washed with diethyl ether (3×20 mL), and dried under vacuo for 2 hours. The crude product was used in the following step without further purification.

Step 3 Preparation of 3N-[2(S)-N-tert-(butyloxy)carbonylamino-3-S-triphenylmethylmercaptopropionyl]amino-2,3-dihydro-2-oxo-5-phenyl-1H-1,4-benzodiazepine A mixture of (±) 2,3-dihydro-2-oxo-3-amino-5-phenyl-1H-1,4-benzodiazepine hydrobromide (146 mg, 0.44 mmol), N-Boc-S-Trityl-L-Cysteine (223 mg, 0.48 mmol), diisopropylethylamine (84 μL, 0.48 mmol) in anhydrous N,N-dimethylformamide (5 mL) at room temp. was treated with 1-ethyl-3-(3-dimethylaminopropyl)carbodiimide hydrogen chloride (93 mg, 0.48 minol) and 1-hydroxybenzotriazole (66.5 mg, 0.49 mmol) and stirred at room temp. overnight. The resulting solution was concentrated under vacuo and the residue dissolved in ethyl acetate and water. The organic extract was washed with brine, dried over anhydrous magnesium sulfate, filtered, and concentrated. The residue was subjected to column chromatography on silica gel eluting with 60% ethyl acetate in hexanes. Collection and concentration of appropriate fractions provided a 1:1 mixture of the required diastereomeric products.

Step 4 Preparation of 3-[N-2(S)-amino-3-mercaptopropionyl-amino]2,3-dihydro-2-oxo-5-phenyl-1H-1,4-benzodiazepine (Compound 2)

To a solution of 3N-[2(S)-N-tert-(butyloxy)carbonylamino-3-S-triphenylmethylmercaptopropionyl]amino-2,3-dihydro-2-oxo-5-phenyl-1H-1,4-benzodiazepine (170 mg, 0.24 mmol) in dichloromethane (3.4 mL) at room temperature, trifluoroacetic acid (1.7 mL) was added. The resultant intensely yellow solution was titrated to colorless by dropwise addition of triethylsilane (~53 μmol). The product mixture was concentrated, and partitioned with 0.1 % aqueous trifluoroacetic acid (20 mL) and hexane (20 mL). The organic layer was decanted and the aqueous layer repeatedly extracted with hexane (4 times). The aqueous solution was lyophilized overnight and the residue (73 mg) was subjected to high pressure liquid chromatography on a C-18 Vydac protein-peptide column (1 in) eluting with 95% (0.1% trifluoroacetic acid in water)/5% (0.09% trifluoroacetic acid in acetonitrile to 40% (0.1% trifluoroacetic acid in water)/60% (0.09% trifluoroacetic acid in acetonitrile 45 minutes linear gradient. Pure fractions of each diastereomers were collected and lyophilized to provided the pure faster and slower eluting diastereomers.

Anal. Calcd for $C_{18}H_{18}N_4O_2S \cdot 1.45$ $CF_3COOH \cdot 0.45$ $H_2O$: C, 47.56; H, 3.89; N, 10.61. Found: C, 47.61; H, 4.02; N, 10.24 for the faster eluting isomer.

Example 3
In Vitro Inhibition of Ras Farnesyl Transferase

Farnesyl-protein transferase (FTase) from bovine brain was chromatographed on DEAE-Sephacel (Pharmacia, 0–0.8 M NaCl gradient elution), N-octyl agarose (Sigma, 0–0.6 M NaCl gradient elution), and a mono Q HPLC column (Pharmacia, 0–0.3 M NaCl gradient). Ras-CVLS at 3.5 μM, 0.25 μM [³H]FPP, and the indicated compounds were incubated with either a partially purified bovine enzyme preparation or a recombinant human enzyme preparation. The recombinant human enzyme was prepared as described in Omer, C. A., Kral, A. M., Diehl, R. E., Prendergast, G. C., Powers, S., Allen, C. M., Gibbs, J. B. and Kohl, N. E. (1993) *Biochemistry* 32:5167–5176. The FTase data presented below in Table 1 reflects the ability of the test compound to inhibit RAS farnesylation in vitro, as described in Pompliano, et al. *Biochemistry* 31:3800 (1992).

TABLE 1

Inhibition of RAS farnesylation by compounds of this invention*

| Compound | IC$_{50}$(μM)* |
|---|---|
| 1 - faster eluting isomer | 2.6 μM |
| 1 - slower eluting isomer | 0.11 μM |
| 2 - faster eluting isomer | 1.6 μM |
| 2 - slower eluting isomer | 42 μM |

*(IC$_{50}$ is the concentration of the test compound which gives 50% inhibition of FTase under the described assay conditions)

What is claim is:

1. A compound of the formula I:

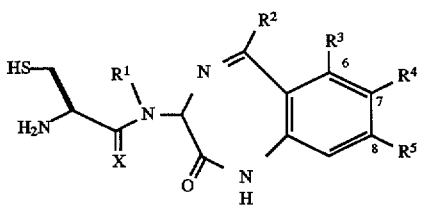

I or a pharmaceutically acceptable salt or disulfide thereof wherein:

R$^1$ is selected from: H or C$_{1-4}$ alkyl;

R$^2$ is selected from: H; unsubstituted or substituted C$_{1-4}$ alkyl, unsubstituted or substituted C$_{3-6}$ cycloalkyl, unsubstituted or substituted heterocycle, unsubstituted or substituted aryl, wherein the substituent is selected from:

a) C$_{1-4}$ alkoxy,
b) aryl or heterocycle,
c) halogen,
d) HO,
e) ![](R^6 carbonyl), or
f) —SO$_2$R$^6$;

R$^3$, R$^4$ and R$^5$ are independently selected from: H, C$_{1-4}$ alkyl, and halogen; provided that R$^2$ is H when R$^3$ is other than H;

R$^6$ is C$_{1-4}$ alkyl or aralkyl;

X is O or H$_2$.

2. The compound according to claim 1 having the formula I:

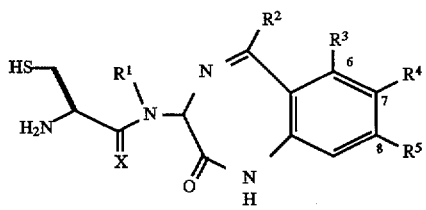

I or a phrmaceutically acceptable salt or disulfide thereof, wherein:

R$^1$ is C$_{1-4}$ alkyl;

R$^2$ is selected from: H; unsubstituted or substituted C$_{1-4}$ alkyl, unsubstituted or substituted C$_{3-6}$ cycloalkyl or unsubstituted or substituted aryl, wherein the substituent is selected from:

a) C$_{1-4}$ alkoxy,
b) aryl or heterocycle,
c) halogen,
d) HO,
e) ![](R^6 carbonyl), or
f) —SO$_2$R$^6$;

R$^3$, R$^4$ and R$^5$ are independently selected from: H, C$_{1-4}$ alkyl, and halogen; provided that R$^2$ is H when R$^3$ is other than H;

R$^6$ is C$_{1-4}$ alkyl or aralkyl;

X is O or H$_2$.

3. A compound which is selected from:

3-[2(S)-amino-3-mercaptopropionyl-N-methylamino]-2,3-dihydro-2-oxo-5-phenyl-1H-1,4-benzodiazepine 3-[2(S)-amino-3-mercaptopropionyl-N-methylamino]-2,3-dihydro-2-oxo-5-(2-naphthyl)-1H-1,4-benzodiazepine 3-[2(S)-amino-3-mercaptopropionyl-N-methylamino]-2,3-dihydro-2-oxo-5-(1-naphthyl)-1H-1,4-benzodiazepine 3-[2(S)-amino-3-mercaptopropionyl-N-methylamino]-7,8-dimethyl-2,3-dihydro-2-oxo-5-phenyl-1H-1,4-benzodiazepine 3-[N-2(S)-amino-3-mercaptopropionyl-N-methylamino]-2,3-dihydro-6-naphthylmethyl-2-oxo-1H-1,4-benzodiazepine 3-[2(S)-amino-3-mercaptopropionyl-N-methylamino]-2,3-dihydro-2-oxo-5-(8-quinolinyl)-1H-1,4-benzodiazepine 3-[2(S)-amino-3-mercaptopropionyl-N-methylamino]-2,3-dihydro-2-oxo-5-(2,3-dimethylphenyl)-1H-1,4-benzodiazepine or a pharmaceutically acceptable salt or disulfide thereof.

4. The compound according to claim 1 which is:

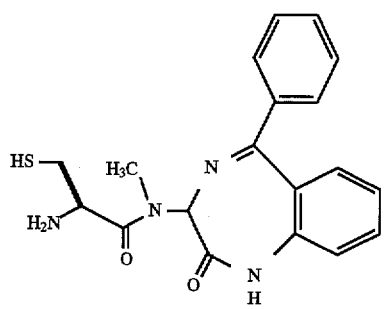

3-[2(S)-amino-3-mercaptopropionyl-N-methylamino]-2,3-dihydro-2-oxo-5-phenyl-1H-1,4-benzodiazepine or a pharmaceutically acceptable salt or disulfide thereof.

5. A pharmaceutical composition comprising a pharmaceutical carrier, and dispersed therein, a therapeutically effective amount of a compound of claim 1.

6. A method for inhibiting farnesyl-protein transferase which comprises administering to a mammal in need thereof a therapeutically effective amount of a composition of claim 5.

* * * * *